United States Patent
Hills et al.

(10) Patent No.: US 6,395,295 B1
(45) Date of Patent: May 28, 2002

(54) USE OF SURFACE ACTIVE AGENT FOR THE MANUFACTURE OF A MEDICAMENT FOR TREATMENT OF DISORDERS OF THE MIDDLE EAR

(75) Inventors: Brian Andrew Hills, Queensland (AU); Derek Alan Woodcock, Berkhampstead (GB)

(73) Assignee: Britannia Pharmaceuticals Limited, Surrey (GB)

(*) Notice: Subject to any disclaimer, the term of this patent is extended or adjusted under 35 U.S.C. 154(b) by 0 days.

(21) Appl. No.: 09/582,346
(22) PCT Filed: Nov. 26, 1998
(86) PCT No.: PCT/GB98/03526
§ 371 (c)(1), (2), (4) Date: Oct. 20, 2000
(87) PCT Pub. No.: WO99/33472
PCT Pub. Date: Jul. 8, 1999

(30) Foreign Application Priority Data

Dec. 24, 1997 (GB) .............................................. 9727275
Jan. 21, 1998 (GB) .............................................. 9801328

(51) Int. Cl.$^7$ ........................ A61P 27/16; A61K 31/685
(52) U.S. Cl. ........................ 424/437; 424/502; 514/78
(58) Field of Search ................... 424/437, 502; 514/78

(56) References Cited

U.S. PATENT DOCUMENTS

5,299,566 A  4/1994  Davis et al. ............ 128/200.24

FOREIGN PATENT DOCUMENTS

| EP | 0119056 | 9/1984 |
| EP | 0528034 | 2/1993 |
| WO | WO9729738 | 8/1997 |

OTHER PUBLICATIONS

Andrew J. Nemechek e tal. "Nebulized Surfactant for Experimentally Induced Otitis Media with Effusion", Otolaryngology Head and Neck Surgery, Nov. 1997, 117:475–479.

Sandra L. Wheeler et al. "Rat Eustachian Tube Synthesizes Disaturated Phosphatidylcholine", BBA Report, Biochimica et Biophysica Acta 794:348–349, 1984.

Primary Examiner—Edward J. Webman
Assistant Examiner—Helen Nguyen
(74) Attorney, Agent, or Firm—Roylance, Abrams, Berdo & Goodman, L.L.P.

(57) ABSTRACT

The invention relates to the treatment of serous otitis media (glue ear). A medicament is disclosed which comprises a surface active phospholipid (SAPL) which is instilled as a powder into the middle ear. The SAPL has an affinity for the surface of the Eustachian tube and forms a film over its surface which prevents or deters reblockage of the tube.

14 Claims, 2 Drawing Sheets

USE OF SURFACE ACTIVE AGENT FOR THE MANUFACTURE OF A MEDICAMENT FOR TREATMENT OF DISORDERS OF THE MIDDLE EAR

This invention relates to medicaments for use in the treatment of disorders of the middle ear.

It is important to maintain the patency of the Eustachian tubes of the ear since failure to do so can lead to a number of clinical disorders. Blockage of the Eustachian tubes often occurs in persons experiencing discomfort arising from changes in ambient pressure, such as aviators and divers, and this can lead to pain and damage to the hearing. Partial or total blockage of the Eustachian tube can potentiate the onset of serous otitis media (more commonly known as glue ear), which is a very common disorder in children in the age range of about 7 to 12. This can cause partial deafness leading to lack of attention in school and developmental problems.

Currently, the only available procedure for dealing with the problem of glue ear is to fit grommets or ventilation tubes, although antibiotics can offer short-term relief. Grommets are small plastic tubular inserts which require to be inserted by a surgical procedure involving an incision in the tympanic membrane. The procedure has disadvantages, quite apart from the need for a surgical procedure, including the risk of infection in the middle ear arising from direct contact with a contaminated environment and the requirement that the patient must avoid getting water in the treated ear, thus excluding the child from all aquatic activities. A further problem is that grommets tend to fall out.

It is also believed that the exudation of serous fluid can cause plug formation to occur in the Eustachian tube in adults which can cause obstruction to air flow and thus prevent ventilation of the middle ear. This problem has major implications in underwater diving activities, aviation and emergency escape from submarines. This is also an area which is addressed by the present invention.

The present invention is based upon the belief that in the healthy natural ear, the surfaces of the Eustachian tubes contain a natural lining or coating which provides easy release, thus preventing or deterring the surfaces of the tubes from sticking together. The present invention, therefore, seeks to overcome the problems discussed above by administering a medicament capable of providing the same kind of action as the natural release agent in circumstances where the natural release agent has failed or is not deficient.

According to one aspect of the present invention there is provided use of a surface active agent composition in the preparation of a medicament as a prophylactic or for treatment of disorders of the middle ear by administration to the Eustachian tube of the medicament, said composition including a component capable of persisting on the surface of the Eustachian tube for an extended period of time.

Preferably, the surface active agent should be capable of persisting on the surface of the Eustachian tube for at least about 3 months, preferably at least 6 months, so that the tube will retain a surface active layer over such an extended period and will be less likely to block. Surface active agents are preferably solid and capable of forming an adherent layer on the surface of the tube. A physical or chemical binding of the surfactant to the surface of the Eustachian tube is highly desirable. The surface active agent may be selected from a variety of materials but should have a very low level of toxicity. Examples of suitable surface active agents are soaps, e.g. a fatty acid salt, such as magnesium stearate. Preferred surface active agents include surface active phospholipids, such as diacyl phosphatidyl cholines (DAPC's), e.g. dipalmitoyl phosphatidyl choline (DPPC); dioleyl phosphatidyl choline (DOPC) and distearyl phosphatidyl choline (DSPC). It is also preferred to include a spreading agent in the composition to assist the DPPC or analogous compound rapidly to form a thin film over the surface of the Eustachian tube. A number of agents are capable of acting in this way including other phospholipids, such as phosphatidylglycerols (PG); phosphatidylethanolamines (PE); phosphatidylserines (PS) and phosphatidylinositols (PI). Another useful spreading agent is cholesteryl palmitate (CP).

According to another aspect, therefore, the present invention comprises use of a surface-active phospholipid (SAPL) composition in the preparation of a medicament as a prophylactic or for treatment of disorders of the middle ear, by administration to the Eustachian tube (or its aural end) of the SAPL composition in finely-divided solid form, said composition including a component capable of binding to the surface of the Eustachian tube.

BRIEF DESCRIPTION OF THE DRAWINGS

Unsaturated phosphatidyl glycerol (PG) is believed to be capable of binding to the surface of the Eustachian tube and is, therefore, a preferred component of the SAPL. Dipalmitoyl phosphatidyl choline (DPPC) may function also in this way and is also a preferred compound of the SAPL. PG has a further important function in medicaments employed in the present invention which is its ability to cause the DPPC to form a dry powder. The particle size of such powders is not critical and the controlling factor is that the size is preferably such that medicament can be readily instilled into the patient's ear. Generally, the particle size is within the range of 0.5 to 100 $\mu$m Particles which are more readily conveyed in a gas stream have a particle size of from 0.5 to 20 $\mu$m, preferably 0.5 to 10 $\mu$m and more preferably 0.5 to 2 $\mu$m. Finely-divided dry powders of this kind are believed to be absorbed very rapidly onto the surfaces of the Eustachian tube, i.e. bound to the epithelium. Preferably, the SAPL compositions employed in the present invention are blends of dipalnitoyl phosphatidyl choline (DPPC) and PG, although as indicated above, other phospholipids may be employed.

The medicament should generally be essentially free from animal protein in order to avoid the danger of patient sensitivity to animal proteins. Also, animal proteins may become adhesive and, for this reason, should preferably be excluded from the compositions.

DPPC can be prepared synthetically by the use of acyl chlorides using the method of Baer & Bachrea—Can. J. Of Biochem. Physiol 1959; 37, page 953 and is available commercially from Sigma (London) Ltd. The PG may be prepared from egg phosphatidyl choline by the methods of Comfurions et al and Dawson, Biochem. Biophys Acta 1977; 488; pages 36–42 and Biochem J. 1947; 192; pages 205–210.

The medicaments employed in the present invention are generally finely-divided dry powders having a particle size distribution which is small enough to be introduced into the middle ear in a gas stream from a dispersion device. Generally, medicaments are preferred in which the particle size distribution is such that a major proportion is between 0.5 and 2 $\mu$m. The medicament of the present invention may be introduced into the middle ear through a cannula, e.g. connected to a syringe, while making a second hole in the tympanic membrane to allow air to escape from the middle ear and avoiding undue pressure in the middle-ear cavity.

Figure 1:
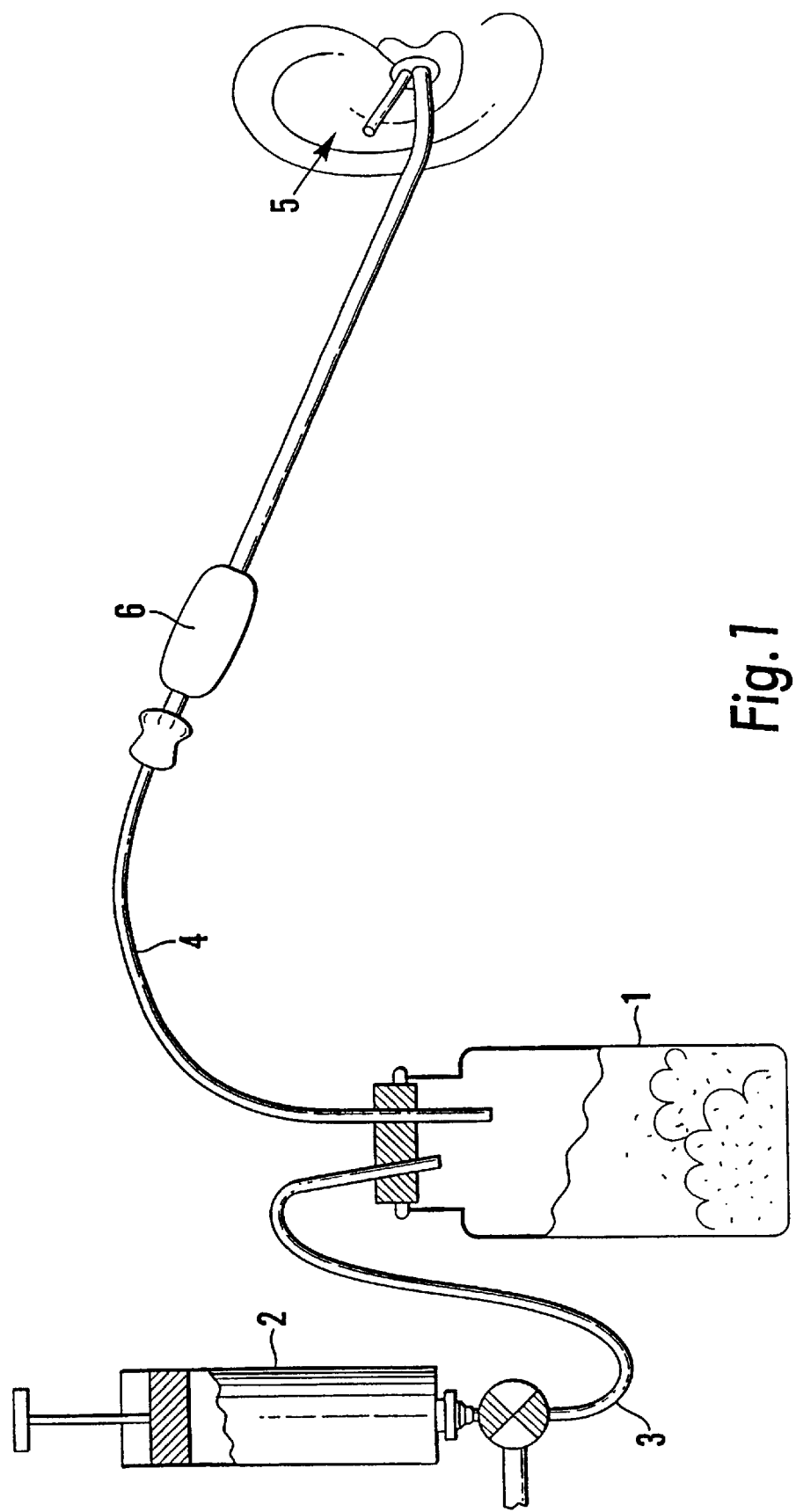
Figure 2:
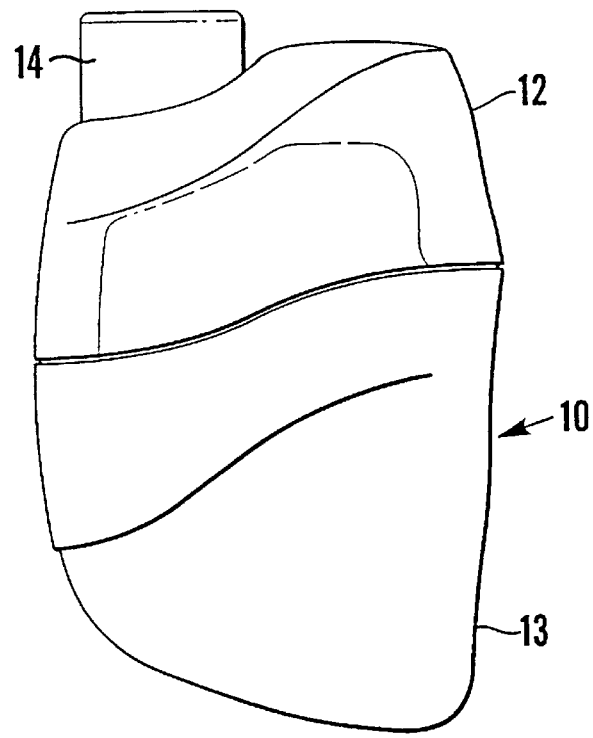
Figure 3:
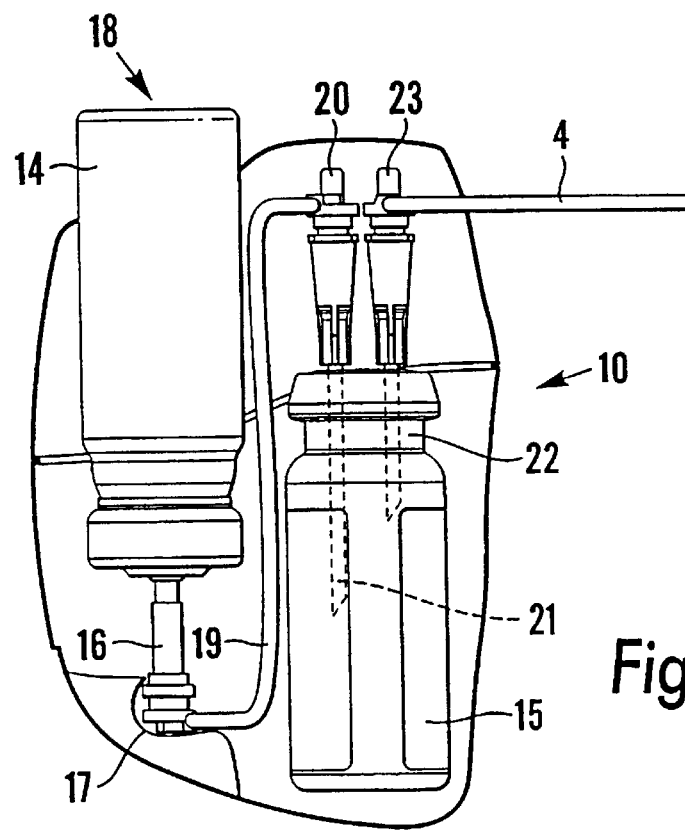

In the accompanying drawings, FIG. 1 is a diagrammatic representation of suitable apparatus for administering the surface active agent. The medicament, such as a powdered blend of DPPC and PG is contained in a vial (1). A syringe (2) is connected by a tube (3) to the vial so that powder can be atomised in the vial and displaced along a catheter (4) to the patient's ear (5). A conventional tool (6) for cleaning the ear may be slidable on the catheter (4). A hole is pierced in the tympanic membrane to gain access to the middle ear and a second hole is made with a hollow needle to allow air to escape. By operating the syringe, amounts of powdered surfactant are instilled into the ear. Using the apparatus shown in the drawing, a downward stroke of the syringe caused about 1 ml of powder to be blown into the middle ear.

More complex dispersion devices may also be employed to introduce the medicament. These may employ a propellant such as a halocarbon to form a gas stream and may include a tapered discharge nozzle, baffle or venturi to accelerate particles through a discharge nozzle and to remove oversize particles. Suitable halocarbons include hydrofluorocarbons, hydrofluorochlorocarbons and fluorochloro-carbons having a low boiling point, such as those marketed by DuPont under the trade marks "Freon" and "SUVA". Pharmaceutically acceptable hydrofluoroalkanes are available as HFA-134a and 227.

A more sophisticated design of dispensing device for administering the powdered medicament to the middle ear is shown in FIGS. 2 and 3 in which:

FIG. 2 is a side elevation of the dispenser; and

FIG. 3 is a similar view, but shows its interior.

Referring to FIGS. 2 and 3, a casing (10) is formed from two plastic mouldings (12 & 13) which snap together to form a container for a pressurised canister (14) and a vial (15). Canister (14) contains a low boiling liquid, preferably a hydrofluorocarbon such as HFA-134a or HFC-227, under sufficient pressure to maintain the propellant liquid at normal room temperature. Vial (15) contains the powdered medicament, such as "Alec". Canister (14) has a release valve (16) which is received in a recess (17) so that finger pressure on the inverted end (18) of the canister will cause propellant to be released into a tube (19). Tube (19) is typically a hard plastics, e.g. pvc or polypropylene, tube of about 2~3 mm outside diameter and about 0.5 to 2 mm inside diameter. Tube (19) connects valve (16) with a fitting (20) and thence to a tube or needle (21) which extends into the vial (15). Vial (15) may be closed with a rubber seal which is penetrated by the tube or needle (21) and self-seals around the tube or needle. A second needle or tube (22) extends part way into the vial through the rubber seal in the neck of the vial and connects with a fitting (23). Fitting (23) discharges into a catheter (4) which is inserted through a tool (6) into the middle ear, as indicated in FIG. 1. The advantage of the dispenser shown in FIGS. 2 and 3 is that it can be operated 'one-handed' while the doctor or nurse ensures that the catheter is correctly positioned in the patient's ear.

In general, the DPPC and PG may be present in a weight ratio of from 9:1 to 1:9. Compositions employed in current formulations have been in the weight ratio of from about 6:4 to 8:2.

Because we are concerned in the present invention to achieve a long-term adsorption of the medicament onto the surface of the middle ear, it is highly desirable that the SAPL (or its active component) should not break down in the environment of the ear. One of the factors which will reduce the life of a release lining or coating will be the presence of enzymes capable of digesting DPPC and/or PG. Such enzymes only attack the laevo rotatory (L) forms, which constitutes the naturally occurring form. Therefore, the medicament should preferably contain the dextro rotatory (D form) or at least comprise a racemic mixture which is obtained by synthetic preparation routes. This also applies to the other SAPL/s mentioned above.

In current studies in the treatment of glue ear, the method employed was as follows. Under general anaesthesia, myringotomy was performed and serous fluid (glue) suctioned from the middle ear. An SAPL in powder form available from Britannia Pharmaceuticals Limited of Brighton Road, Redhill, Surrey, England, under the trade mark "Alec" was instilled into the middle ear through a small hole formed in the tamponeal membrane. 'Alec' is a mixture of DPPC and PG in the weight ratio of DPPC:PG of about 70:30 which has a particle size in the range of 0.5 to 2 $\mu$m and a median particle size of about 1.2 $\mu$m. A second small hole was made in the membrane in order to reduce the likelihood of building up excessive pressure with undesirable sequelae. The apparatus employed was similar to that shown in the accompanying drawing.

Using the above described apparatus, approximately 5 puffs were applied to one ear of 14 children diagnosed as having severe glue ear. As a result, about 10~30 mg of 'Alec' were instilled into each of the treated ears. The other ear was fitted with a grommet in accordance with standard ENT practice. After 6 months, all patients were tested for hearing acuity by standard audiometric procedures. The results were as follows:

| Parameter | Grommets (n = 14) | Alec (n = 14) |
|---|---|---|
| Audiometry | 5 cases superior to Alec | 7 cases superior to grommets |
| No. of successes | 14 | 13 (4 excellent, 9 moderate) |

The above comparative tests show that grommets and "Alec" are both effective in treating hearing loss arising from glue ear. Although grommets were successful in all children tested in the sense that pressure was relieved and normal hearing restored, the procedure of the present invention can be regarded as advantageous because it avoids the disadvantages of fitting grommets as mentioned above.

A procedure which is successful in a majority of cases with minor surgical involvement, therefore provides significant advantages over the prior methods. The procedure of the present invention can also be carried out prophylatically before significant build-up of glue occurs in the ear.

In a broader sense, it can also be used prophylatically for other disorders or to avoid conditions such as experienced by divers or aviators as described above, when subjected to substantial changes in air pressure.

SAPL compositions have been used extensively as a lung-expanding agent in premature neonates and no significant contraindications have been observed. High dosage rates and prophylatic use of the compositions can, therefore, be safely adopted.

It may be advantageous to include other substances into the medicament, such as anti-fungal or anti-bacterial agents.

What is claimed is:

1. A method for the prophylaxis or treatment of disorders of the middle ear which comprises administering a solid, particulate composition by direct instillation to the Eustachian tube, said composition consisting essentially of one or more surface active phospholipids (SAPL) including a component that binds to the surface of the Eustachian tube.

2. The method according to claim 1, in which said component persists on the surface of the Eustachian tube for at least three months.

3. The method according to claim 1, in which said composition is of a particle size distribution for introduction into the middle ear in a gas stream.

4. The method according to claim 3, in which a gas stream comprises a gaseous halocarbon.

5. The method according to claim 1, wherein the majority of the particles in said composition are between about 0.5 μm and about 100 μm.

6. The method according claim 1, in which said composition comprises a blend of dipalmitoyl phosphatidyl choline (DPPC) and phosphatidyl glycerol (PG).

7. The method according to claim 6, in which the PG is present in an amount that renders the DPPC as a dry powder at normal room temperature.

8. The method according to claim 6, in which the DPPC and PG are present in a weight ratio of from about 9:1 to 1:9.

9. The method according to claim 8, in which the DPPC and PG are present in a weight ratio of from about 6:4 to 8:2.

10. The method according to claim 7, in which the composition is prepared by forming a solution of the DPPC and PG in a common solvent and recovering particles from the solution containing a mixture of DPPC and PG.

11. The method according to claim 1, in which the SAPL component or components are in the D or DL form.

12. A method for treating glue ear which comprises instilling directly into the middle ear a solid particulate composition which is a blend of dipalmitoyl phosphatidyl choline (DPPC) and phosphatidyl glycerol (PG).

13. The method according to claim 12, in which the majority of the particles in said composition have a particle size within the range of about 0.5 μm to about 5 μm.

14. The method according to claim 12, in which the DPPC and PG are present in a weight ratio from 6:4 to 8:2.

* * * * *